(12) United States Patent
Een et al.

(10) Patent No.: US 8,282,615 B2
(45) Date of Patent: Oct. 9, 2012

(54) ABSORBENT ARTICLE WITH LEAK BARRIERS

(75) Inventors: Hans Een, Mölnlycke (SE); Jan Wästlund-Karlsson, Mölndal (SE); Ulrika Carlson, Billdal (SE); Sue Uner, Folsom, PA (US)

(73) Assignee: SCA Hygiene Products AB, Göteborg (SE)

( * ) Notice: Subject to any disclaimer, the term of this patent is extended or adjusted under 35 U.S.C. 154(b) by 413 days.

(21) Appl. No.: 12/594,888

(22) PCT Filed: Apr. 11, 2007

(86) PCT No.: PCT/SE2007/000340
§ 371 (c)(1),
(2), (4) Date: Oct. 6, 2009

(87) PCT Pub. No.: WO2008/127152
PCT Pub. Date: Oct. 23, 2008

(65) Prior Publication Data
US 2010/0137825 A1  Jun. 3, 2010

(51) Int. Cl.
*A61F 13/15* (2006.01)
(52) U.S. Cl. ......... 604/385.24; 604/385.21; 604/385.23; 604/385.28
(58) Field of Classification Search ............ 604/385.28, 604/385.21, 385.23, 385.24
See application file for complete search history.

(56) References Cited

U.S. PATENT DOCUMENTS

| | | |
|---|---|---|
| 4,695,278 A | 9/1987 | Lawson |
| 4,936,839 A | 6/1990 | Molee et al. |
| 5,167,653 A | 12/1992 | Igaue et al. |
| 5,575,785 A | 11/1996 | Gryskiewicz et al. |
| 5,667,609 A | 9/1997 | Liu |
| 5,827,253 A | 10/1998 | Young et al. |
| 6,102,892 A | 8/2000 | Putzer et al. |
| 6,620,145 B2 | 9/2003 | Nakaoka et al. |

(Continued)

FOREIGN PATENT DOCUMENTS

EP  0 219 326 A2  4/1987
(Continued)

OTHER PUBLICATIONS

International Search Report for PCT/SE2007/000340 completed Dec. 19, 2007.
(Continued)

*Primary Examiner* — Lynne Anderson
*Assistant Examiner* — Bradley Philips
(74) *Attorney, Agent, or Firm* — Buchanan Ingersoll & Rooney PC (57) ABSTRACT

An absorbent article includes a front region (2), a back region (3) and a crotch region (4) there between. The article further includes substantially longitudinally extending inner (12) and outer (13) leak barriers alongside each side of the absorbent core (9). The inner and outer leak barriers are spaced from each other in the transverse direction (x) of the article. The inner leak barriers (12) extend at least along the part of the crotch region (4) having the narrowest width (w1) in the transverse direction (x), and along a length (b) of at least 5 cm, and the outer leak barriers (13) extend along at least a part of the front region (2) and/or back region (3) of the article, while at least a part of the crotch region (4) along which said inner leak barriers (12) extend is free from raised outer leak barriers (13).

22 Claims, 5 Drawing Sheets

U.S. PATENT DOCUMENTS

| | | | |
|---|---|---|---|
| 7,150,732 B2 * | 12/2006 | Yoshida et al. | 604/389 |
| 2001/0018580 A1 | 8/2001 | Suzuki et al. | |
| 2002/0087140 A1 * | 7/2002 | Otsubo | 604/385.28 |
| 2003/0114827 A1 | 6/2003 | Peterson | |
| 2003/0139724 A1 | 7/2003 | Ragnarson et al. | |
| 2003/0171732 A1 | 9/2003 | Heyrman et al. | |
| 2004/0127882 A1 | 7/2004 | Weber | |
| 2004/0133181 A1 * | 7/2004 | Ishiguro et al. | 604/385.28 |
| 2006/0142723 A1 * | 6/2006 | Kuroda et al. | 604/385.04 |
| 2006/0149207 A1 * | 7/2006 | Turi et al. | 604/385.19 |
| 2007/0233034 A1 | 10/2007 | Hildeberg et al. | |
| 2007/0293833 A1 | 12/2007 | Wennerback | |
| 2009/0088718 A1 * | 4/2009 | Toyoshima et al. | 604/385.23 |

FOREIGN PATENT DOCUMENTS

| | | |
|---|---|---|
| EP | 0 304 957 A2 | 3/1989 |
| EP | 0 913 137 A2 | 5/1999 |
| EP | 1 035 818 B1 | 4/2002 |
| EP | 1 384 459 A2 | 1/2004 |
| EP | 0 969 784 B1 | 2/2004 |
| FR | 2 810 879 A1 | 1/2002 |
| GB | 2 284 538 A | 6/1995 |
| JP | 2-174845 A | 7/1990 |
| JP | 2002-58703 A | 2/2002 |
| JP | 2006-51269 A | 2/2006 |
| WO | WO 97/29722 A1 | 8/1997 |
| WO | WO 02/49560 A1 | 6/2002 |
| WO | WO 2004/060251 A1 | 7/2004 |
| WO | WO 2005/122985 A1 | 12/2005 |
| WO | WO 2006/093439 A1 | 9/2006 |
| WO | WO 2007/114744 A1 | 10/2007 |

OTHER PUBLICATIONS

Written Opinion for PCT/SE2007/000340 completed Dec. 19, 2007.
Extended European Search Report issued on Feb. 15, 2012 by the European Patent Office in corresponding European Patent Application No. 07748006.9.

* cited by examiner

ABSORBENT ARTICLE WITH LEAK BARRIERS

TECHNICAL FIELD

The present invention refers to an absorbent article, such as a diaper, pant diaper, incontinence guard, sanitary napkin and the like intended to absorb and retain body fluid of the wearer, said article comprises substantially longitudinally extending leak barriers.

BACKGROUND OF THE INVENTION

Absorbent articles of the above mentioned kind are known, which have longitudinally extending leak barriers alongside the absorbent structure. These leak barriers, also called containment or barrier flaps, have a free laterally inward elasticized side and a laterally outward side, wherein the elasticized side of the leak barrier is raised from the inner cover of the absorbent article. Such raised leak barriers help to reduce the occurrence of leakage of body exudates from the absorbent articles.

Absorbent articles often have an absorbent core that is narrower in the crotch region. Applying the leak barriers to the article with a distance between the leak barriers that is adapted to the width of the absorbent core in the narrow crotch region may result in a distance between the leak barriers in the front and back regions of the article that is too small, especially for articles having a big difference in width of the absorbent core in the crotch region and the front and back regions respectively.

U.S. Pat. No. 6,620,145 discloses a diaper provided with raised leak barriers, which in the crotch area of the diaper are adhered to the body facing sheet of the article at a location inwardly of the laterally outward side of the leak barrier, so that the raised height of the leakage barrier is less in the crotch region than in the front and back regions of the diaper.

US 2004/0127882 discloses a pant diaper provided with leak barriers having a laterally outward side that follows the contours of the leg openings of the diaper.

WO 97/29722 discloses a method of attaching a leak barrier to an absorbent article in a curved manner. The leak barrier has at least one edge parallel to the longitudinal centerline of the article and is bonded to the article along a juncture line that extends in a curved configuration with respect to the longitudinal centerline of the article.

JP 2002-058703 discloses a method of forming a diaper cover from a rectangular piece of material. Leg holes are cut inside the longitudinal side edges of the piece of material, which is then folded inwards along longitudinal folding lines crossing the holes, so as to create an inwardly directed leg contour in each longitudinal side edge. The inwardly folded portions are elasticized to form leak barriers having a lower height in the crotch area.

JP 2006-051269 discloses a diaper provided with leak barriers having a laterally outward side attached to the outer cover by adhesive lines that follows the contours of the leg openings of the diaper. Thus the space between the leak barriers is narrower in the crotch portion than in the front and back regions.

EP-A-0 913 137 discloses an absorbent article comprising a pair of outer leak barriers and a pair of inner leak barriers. The inner leak barriers extend at least over the crotch portion of the article and the outer leak barriers extend over the entire length of the article.

OBJECT AND MOST IMPORTANT FEATURES OF THE INVENTION

One object of the present invention is to provide an absorbent article combining properties of comfort and fit and an effective leakage protection. The article comprises substantially longitudinally extending inner and outer leak barriers at each longitudinal side of the absorbent core, said inner and outer leak barriers being spaced from each other in the transverse direction of the article, wherein the inner leak barriers extend at least along the part of the crotch region having the smallest width in transverse direction, and along a length of at least 5 cm, and the outer leak barriers extend along at least a part of the front region and/or back region of the article, while at least a part of the crotch region along which said inner leak barriers extend is free from raised outer leak barriers.

Further features of the invention are described in the specification below and in the dependant claims.

The invention is especially applicable to an absorbent article in the form of an incontinence guard, a diaper and a pant-type absorbent article and more particularly to such articles having an absorbent core that is considerably narrower in the crotch region than in the front and/or back regions.

DESCRIPTION OF DRAWINGS

The invention will in the following be closer described with reference to some embodiments shown in the accompanying drawings.

DEFINITIONS

Absorbent Article

The term "absorbent article" refers to products that are placed against the skin of the wearer to absorb and contain body exudates, like urine, faeces and menstrual fluid. The invention mainly refers to disposable absorbent articles, which are articles that are not intended to be laundered or otherwise restored or reused as an absorbent article after use.

Inner Liquid Permeable Cover

The inner liquid permeable cover forms the inner cover of the absorbent article and in use is placed in direct contact with the skin of the wearer. The inner liquid permeable cover can comprise a nonwoven material, e.g. spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. The inner liquid permeable cover material may further be composed of tow fibres, which may be bonded to each other in a bonding pattern, as e.g. disclosed in EP-A-1 035 818. Further examples of inner liquid permeable cover materials are porous foams, apertured plastic films etc. The materials suited as inner liquid permeable cover materials should be soft and non-irritating to the skin and be readily penetrated by body fluid, e.g. urine or menstrual fluid. The inner liquid permeable cover may further be different in different parts of the absorbent article.

Outer Liquid Impermeable Cover

The outer liquid impermeable cover forms the outer cover of the absorbent article at least on the core area thereof. The outer liquid impermeable cover can comprise a thin plastic film, e.g. a polyethylene or polypropylene film, a nonwoven material coated with a liquid impervious material, a hydrophobic nonwoven material, which resists liquid penetration, or a laminate, e.g. of a plastic film and a nonwoven material. The outer liquid impermeable cover material may be breathable so as to allow vapour to escape from the absorbent core, while still preventing liquids from passing through. Examples of breathable outer liquid impermeable cover materials are porous polymeric films, nonwoven laminates from spunbond and meltblown layers, laminates from porous polymeric films and nonwoven materials.

Absorbent Core

The absorbent core can be of any conventional kind. Examples of commonly occurring absorbent materials are cellulosic fluff pulp, tissue layers, airlaid materials, highly absorbent polymers (so called superabsorbents), absorbent foam materials, absorbent nonwoven materials or the like. It is common to combine cellulosic pulp fibres with superabsorbent polymers in an absorbent core. Superabsorbent polymers are water-swellable, water-insoluble organic or inorganic materials capable of absorbing at least about 20 times its weight of an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble. Preferred superabsorbent materials are further surface crosslinked so that the outer surface or shell of the superabsorbent particle, fiber, flake, sphere, etc. possesses a higher crosslink density than the inner portion of the superabsorbent. The superabsorbent materials may be in any form suitable for use in absorbent composites including particles, fibers, flakes, spheres, and the like.

A high absorption capacity is provided by the use of high amounts of superabsorbent material. For an absorbent core comprising a matrix of hydrophilic fibers, such as cellulosic fibers, and superabsorbent material, the proportion of superabsorbent material is preferably between 10 and 90% by weight, more preferably between 30 and 70% by weight.

It is conventional in absorbent articles to have absorbent cores comprising layers of different properties with respect to liquid receiving capacity, liquid distribution capacity and storage capacity. These different layers may also have different concentrations of superabsorbent material, so that one layer may have a relatively high concentration of superabsorbent material and another layer a lower concentration, perhaps below 10% by weight superabsorbent material. The thin absorbent bodies, which are common in for example baby diapers and incontinence guards, often comprise a compressed mixed or layered structure of cellulosic fluff pulp and superabsorbent polymers. The size and absorbent capacity of the absorbent core may be varied to be suited for different uses such as for infants or for adult incontinent persons.

The absorbent core may further include an acquisition distribution layer placed on top of the primary absorbent body and which is adapted to quickly receive and temporarily store discharged liquid before it is absorbed by the primary absorbent core. Such acquisition distribution layers are well known in the art and may be composed of porous fibrous waddings or foam materials.

Crotch Point and Crotch Line

Figure 7:
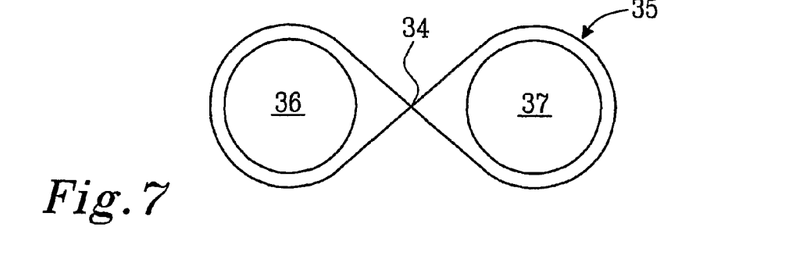
FIG. 7 illustrates how the crotch point of a wearer, an absorbent article and the corresponding absorbent core is determined.

For an absorbent article of the type having a chassis that supports the absorbent core and in which the absorbent core is an integrated part and that is worn around the waist of the wearer, such as a diaper having fastening means attaching the diaper around the waist, a pant-type absorbent article and a belted article having belt members that are attached around the waist, the crotch point is as defined in for example EP-B1-0 969 784. For such article the crotch point is determined by placing the article on a wearer in a standing position and then placing an extensible filament 35 around the legs 36, 37 in a figure eight configuration (FIG. 7). The point in the article and the absorbent core corresponding to the point of intersection of the filament is deemed to be the crotch point 34. It is understood that the crotch point is determined by placing the absorbent article on the wearer in the intended manner and determining where the crossed filament would contact the article/core.

For articles in the form of absorbent pads intended to be placed in the undergarments of the wearer the crotch point 34 is located at the centre, as well transversely and longitudinally, of the narrowest part of the absorbent core.

Figure 1:
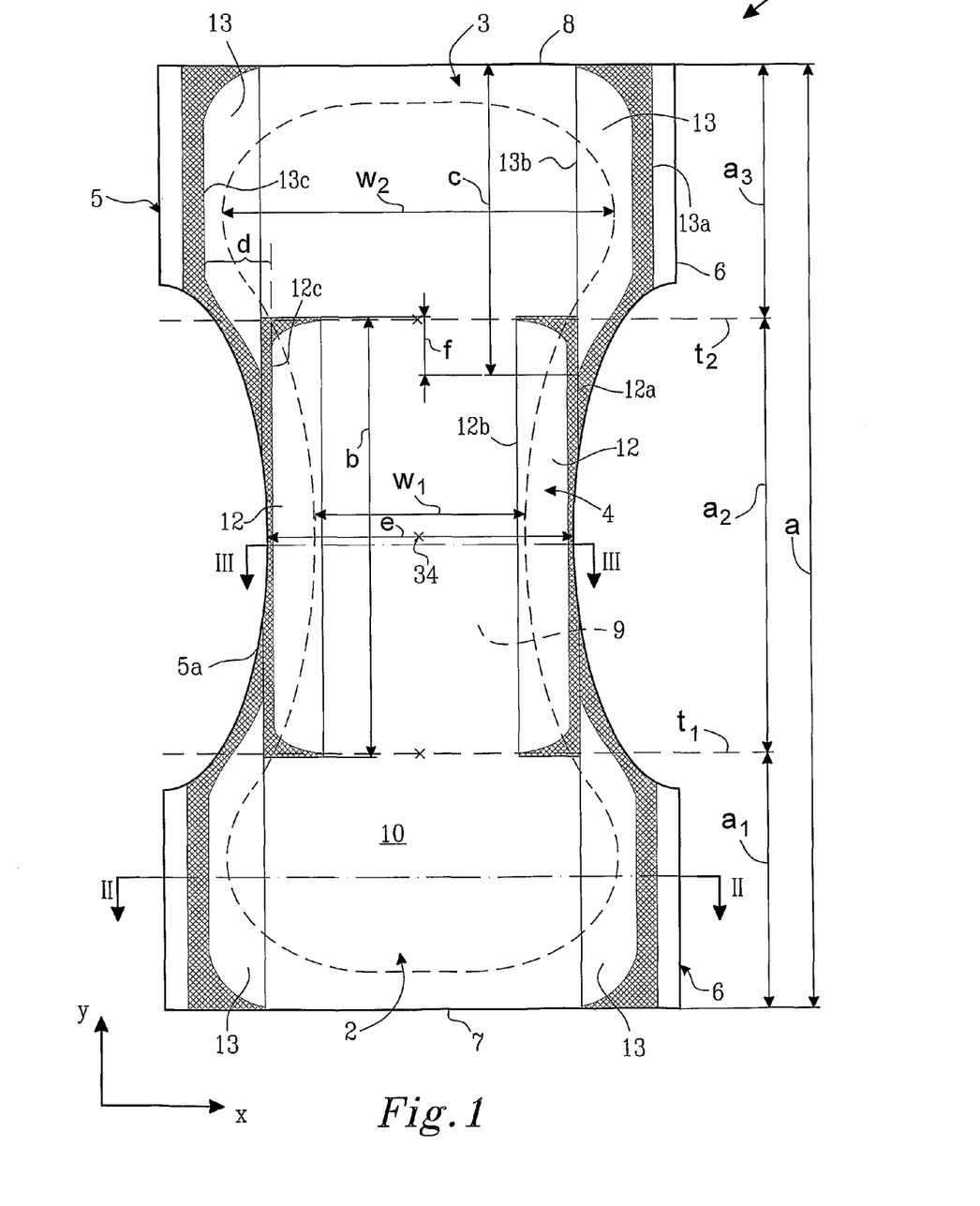
FIG. 1 shows a simplified plan view of an absorbent article in the form of a diaper in its flat, uncontracted state.

The crotch line is a line in the transverse direction, x, of the article/core extending through the crotch point 34, as shown in FIG. 1.

Crotch Region

The crotch region is the narrow part of the article which in use is located between the legs of the wearer and in a normal case the "crotch region" 4 is determined by first locating the crotch point 34 of the absorbent core, and then measuring forward and backward a distance of 25% of the total length of the core. In a case, in which the absorbent core is located asymmetrically in the article, for example the main part of the core is located towards the front of the article and the rear edge of the core is located a distance from the crotch point which is equal to or less than 25% of the total length of the core, the crotch region extends from the rear end of the core, to the crotch point 34 and a distance forwards which is 25% of the total length of the core, or vice versa in case the main part of the core is located towards the back of the article. Thus in the normal case the "crotch region" of the absorbent core corresponds to 50% of the total length of the absorbent core (i.e. in the longitudinal direction, y direction), where the crotch point 34 is located in the longitudinal center of the crotch region. For an asymmetrically placed core, as described above, the crotch region 4 may be shorter than 50% of the total length of the core and the crotch point 34 may be located outside the longitudinal center of the crotch region 4. In FIG. 1 the crotch region 4 is in longitudinal direction defined by the transverse lines $t_1$ and $t_2$.

Front Region

The front region of the absorbent article is defined by the waist edge of the article, the longitudinal side edges of the article, part of the leg openings of the article and the transverse line, $t_1$.

Back Region

The back region is defined in a similar manner: by the waist edge of the article, the longitudinal side edges of the article, part of the leg openings of the article and the transverse line, $t_2$.

Leak Barriers

Leak barriers, or as they also are called containment or barrier flaps, extend substantially longitudinally alongside the absorbent structure. These leak barriers have a free laterally inward elasticized side (distal side) and a laterally outward side (proximal side) attached to the inner cover of the article, wherein the elasticized distal side of the leak barrier is raised from the inner cover of the absorbent article. Such raised leak barriers help to reduce the occurrence of leakage of body exudates from the absorbent articles.

DESCRIPTION OF PREFERRED EMBODIMENTS

FIG. 1 shows a simplified plan view of an absorbent article in a flat, uncontracted state. The absorbent article shown in FIG. 1 is in the form of an incontinence guard intended to be used as a pad in a pair of pants. The article 1 has a longitudinal, y, and a transverse direction, x, and comprises, as seen in its longitudinal direction, a front region 2, a back region 3 and a crotch region 4 there between. The article is defined by a pair of longitudinal side edges 5 and 6 having an inwardly directed leg contour defining leg openings 5a, 6a, and a pair of transverse waist edges 7 and 8.

The front region 2 of the absorbent article is defined by the front transverse waist edge 7 of the article, the longitudinal side edges 5, 6 of the article, part of the leg openings 5a, 6a, of the article and the transverse line $t_1$. The location of the transverse line $t_1$ is determined in a manner as described above, by determining the crotch point 34 of the article and then measuring a selected distance of the absorbent core in longitudinal direction. The front region has an extension in longitudinal direction, y, of the article denoted with $a_1$ in FIG. 1. The back region 3 is defined in a similar manner: by the back waist edge 8 of the article, the longitudinal side edges 5, 6 of the article, part of the leg openings 5a, 6a, of the article and the transverse line $t_2$. The back region 3 has an extension in longitudinal direction, y, of the article denoted with $a_3$ in FIG. 1.

The crotch region 4 is the narrow part of the article which in use is located between the legs of the wearer and is defined on the longitudinal edges by the leg openings 5a, 6a of the article and on the transverse edges by the two transverse lines $t_1$ and $t_2$ described above. The crotch region 4 has an extension in longitudinal direction, y, of the article denoted with $a_2$ in FIG. 1, and is determined in the manner described above by determining the crotch point 34 of the article and then measuring the selected distance of the absorbent core in longitudinal direction.

FIG. 7 illustrates how the crotch point 34 of an absorbent article and of the absorbent core of an absorbent article is determined by placing the article on a wearer in a standing position and then placing an extensible filament 35 around the legs 36, 37 in a figure eight configuration. This method is, as stated above, applicable for absorbent articles of the type having a chassis that supports the absorbent core and that is worn around the waist of the wearer, such as a diaper having fastening means attaching the diaper around the waist, a pant-type absorbent article and a belted article having belt members that are attached around the waist. For absorbent pads however, for example as shown in FIG. 1, which are intended to be worn in the undergarment, the crotch point 34 is defined as the centre, as well transversely and longitudinally, of the narrowest part of the absorbent core.

In its most common form the article comprises an absorbent core 9 and a cover enclosing the absorbent core. Said cover comprises an inner liquid pervious cover 10 on the wearer facing side of the absorbent core 9 and an outer liquid impervious cover 11 on the garment facing side of the absorbent core. The inner liquid pervious cover 10 is often referred to as topsheet, while the outer liquid impervious cover 11 is often referred to as backsheet.

The inner cover 10 and the outer cover 11 extend outwardly beyond the peripheral edges of the absorbent core 9 and have their inner surfaces bonded to each other, e.g. by gluing or welding by heat or ultrasonic. The inner and outer cover materials may further be bonded, e.g. by adhesive, to the absorbent core 9. In an alternative embodiment the inner cover 10 may be eliminated and the absorbent core 9 located directly against the wearer.

The absorbent core 9 in FIG. 1 has a smallest width in the crotch region denoted w1 and a largest width in the back and/or front region denoted w2.

Figure 2:
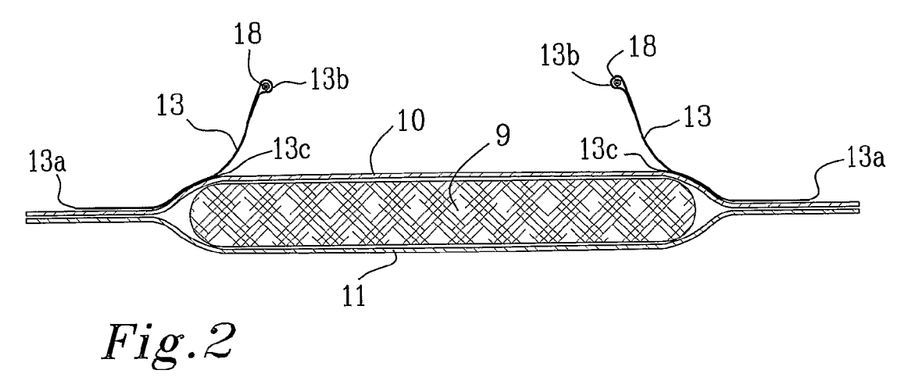
FIG. 2 is a section according to the line II-II in FIG. 1.
Figure 3:
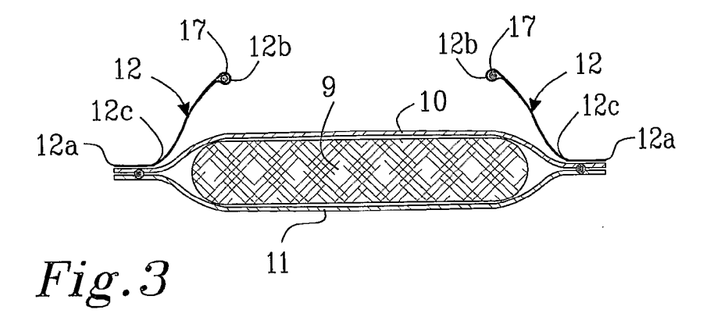
FIG. 3 is a section according to the line III-III in FIG. 1.

The article further comprises longitudinally extending inner and outer elastic leak barriers 12 and 13, spaced from each other in the transverse direction, x, of the article a distance, d, as measured between their respective lines of junction 12c and 13c to the inner cover 10. As can be seen in FIGS. 2 and 3 the inner and outer leak barriers 12 and 13 each has a laterally outward proximal edge 12a and 13a respectively, a laterally inward distal edge 12b and 13b respectively and an elastic member 17 and 18 respectively spacing the respective distal edge away from the inner cover 10. These leak barriers 12 and 13 are at their proximal edges 12a and 13a attached to the inner coversheet 6 close to the lateral edges of the absorbent core 9 either laterally outside the absorbent core 9 or above the absorbent core 9. The attachment is made by for example adhesive, ultrasonic welding or heat bonding. The line of junction of the leak barriers 12 and 13 to the inner cover 10 is denoted with 12c and 13c respectively.

The leak barriers 12, 13 are at their respective transverse end portions laid flat and attached to the inner coversheet also at their distal edges 12b, 13b, for example by adhesive, ultrasonic welding, heat bonding or the like. The leak barriers 12, 13 will herewith form pockets. In FIG. 1 the attached portions of the leak barriers 12, 13 are shadowed.

In FIG. 1 the distal edges 12b and 13b of the leak barriers 12 and 13 are shown in an uncontracted state, in which they are not raised from the inner cover 10. In FIGS. 2 and 3 however the leak barriers 12 and 13 are shown in their raised condition, in which their distal edges 12b and 13b are lifted from the inner cover 10.

The inner leak barriers 12 extend at least along the part of the crotch region 4 having the narrowest width, e, in the transverse direction, x, and along a length, b, of at least 5 cm. It is preferred that the inner leak barriers 12 extend along a length, b, of at least 8 cm, preferably at least 10 cm, more preferably at least 12 cm and most preferably at least 15 cm. The length, b, of the leak barriers is measured as the longitudinal extension of the elasticized distal edges 12b in their flat uncontracted state. The inner leak barriers 12 may extend the entire length of the article. Preferably they do not extend over a length of more than 30 cm and more preferably not more than 25 cm.

The outer leak barriers 13 extend along at least a part of the front region 2 and/or back region 3 of the article, while at least a part of the crotch region 4, along which the inner leak barriers 12 extend is free from outer leak barriers 13. The outer leak barriers 13 may extend all the way to the respective transverse end edge 7 and 8 of the front and back regions respectively, or may alternatively end at a distance inside thereof. The ends of the outer leak barriers 13 facing the crotch region 4 may start in longitudinal direction, y, of the article where the inner leak barriers 12 end, and preferably there is a gap in longitudinal direction, y, of not more than 5 mm between the ends of the inner and outer leak barriers facing each other. The outer leak barriers 13 may extend all the way to the leg openings 5a, 6a. The ends of the inner and outer leak barriers are defined as the ends of the elasticized distal edges 12b and 13b raised from the inner cover. In a preferred embodiment there is no gap in longitudinal direction, y, between the ends of the inner and outer leak barriers facing each other and preferably there is an overlap, f, between them in longitudinal direction. This overlap, f, may vary between 0.5 and 10 cm, preferably between 1 and 5 cm.

The distance, d, in transverse direction, x, between the respective line of junction 12c, 13c, of the inner and outer leak barriers respectively may vary depending on the difference in width of the absorbent core in the crotch region and the front and/or back regions respectively, i.e. the difference between the widths w1 and w2, however preferably the distance d is at least 1 cm. It should be mentioned that the width of the absorbent core in the front and back regions respectively may be the same or different. If the width of the absorbent core is different in the front and back regions the distance d may also be different in the front and back regions. The outer leak barriers 13 may alternatively only be present in either the front or back region.

The invention is primarily applicable to absorbent articles having a considerable difference between w1 and w2. If w2 is measured in the broadest part of the absorbent core, which either can be in the front, the back or both in the front and back regions, w2 should in a preferred embodiment be at least 20% larger than w1, preferably at least 25% larger and more preferably at least 30% larger than w1.

The outer leak barriers 13 are in the embodiment shown in FIG. 1 spaced apart a distance that exceeds the width, e, of the crotch region 4 in the narrowest part thereof. This applies both to the distance between the respective proximal edges 13a and between the respective distal edges 13b. In an alternative embodiment the distance between at least the distal edges 13b of the outer leak barriers 13 is smaller than the narrowest crotch width, e.

Figure 4:
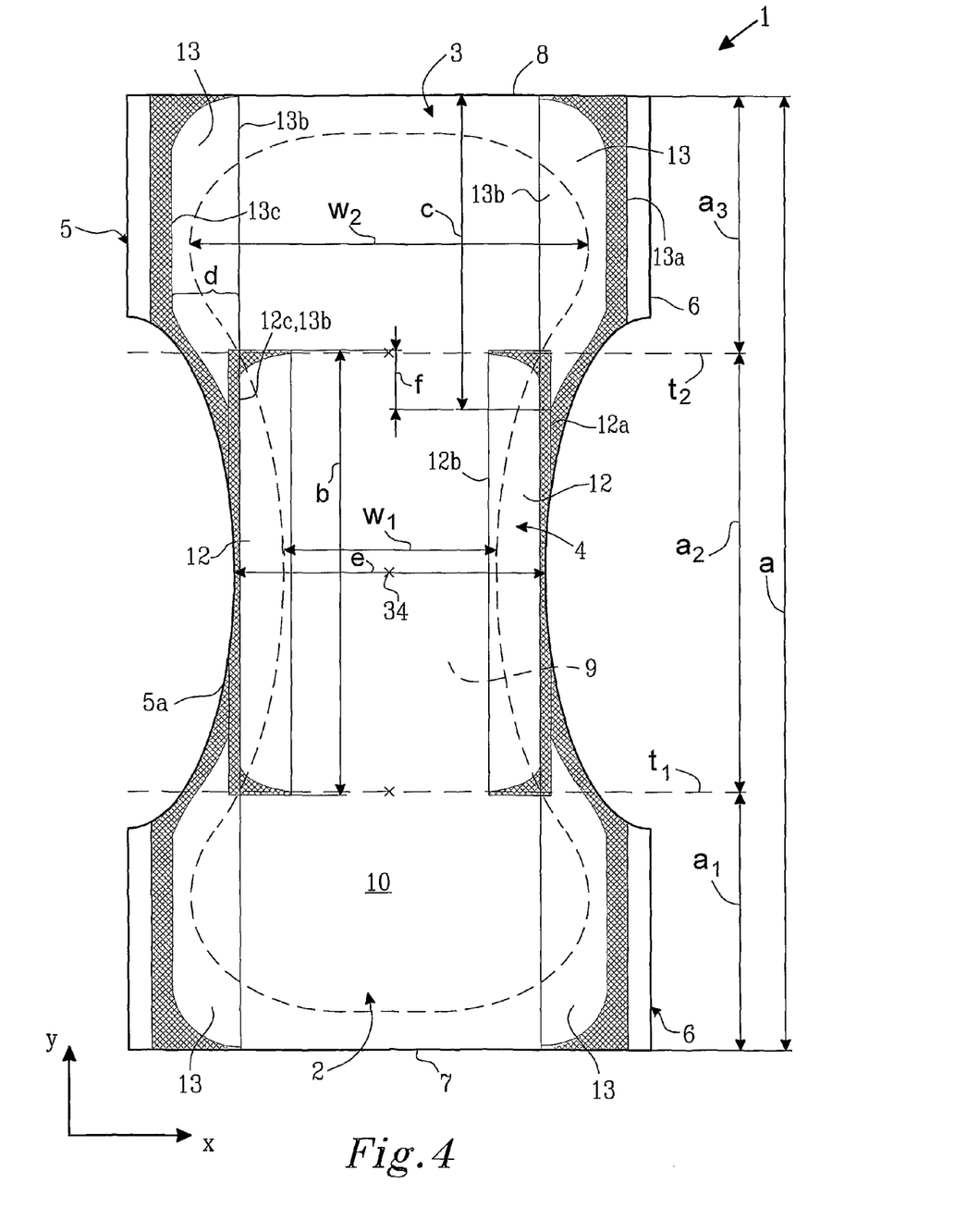
FIG. 4 is a plan view of an absorbent article similar to FIG. 1 but showing a modified embodiment.

In a still further embodiment, illustrated in FIG. 4, the distance between the distal edges 13b of the outer leak barriers 13 is smaller than the narrowest crotch width, e, and the distal edges, including the elastic member 18, extend the entire length of the crotch region $a_2$, and are deactivated by being laid flat and attached to the inner cover 10 of the article in at least the part of the crotch region having the narrowest crotch width, thus preventing the outer leak barriers 13 to raise in said area. The elasticized distal edges 13b of the outer leak barriers 13 will instead form leg elastics in the leg opening area, thus making the provision of additional leg elastic elements redundant. It may also be possible that the distance between the distal edges 13b of the outer leak barriers 13 is slightly larger than the narrowest crotch width, e, so that said distal edges 13b, including the elastic member 18, of the outer leak barriers 13 do not extend along the entire length of the crotch region, $a_2$, but only along the part of the crotch region $a_2$, which is located outside and is broader than the narrowest part thereof. A region adjacent the narrowest crotch width will in this case be free from the leg elastics provided by the elasticized distal edges of the outer leak barriers.

In case leg elastics are provided by the elasticized distal edges 13b of the outer leak barriers 13, which are attached to the inner cover in the crotch region of the article, they should be present in said state, in which they may function as leg elastics, along a length of at least 5 cm in the crotch region.

The distance between the proximal edge 12a and the distal edge 12b of each inner leak barrier 12 should not be more than half the narrowest crotch width, i.e. not more than ½×e.

The distance between the proximal edges 12a, 13a of the respective leak barriers 12, 13 as well as the distance between their distal edges 12b, 13b and the distance between their lines of junction 12c, 13c, is measured when in their uncontracted state lying flat against the inner coversheet 10. The crotch width is also being measured with the diaper is in an uncontracted state as shown in FIG. 1.

The inner and outer leak barriers 12 and 13 may have the same height, as measured between their distal edge 12b, 13b and the respective line of junction 12c, 13c. Alternatively the height of the outer leak barriers 13 is larger than the height of the inner leak barriers. In a still further embodiment the inner leak barriers 12 are higher then the outer leak barriers 13. The outer leak barriers in the 13 in the front and back regions 2 and 3 may have the same height, or the outer leak barriers may be higher in the front region 2 than in the back region, or be higher in the back region 3 than in the front region 2. The inner leak barriers 12 preferably have a height between 1 and 5 cm, while the outer leak barriers 13 preferably have a height between 1 and 8 cm.

The inner and outer leak barriers 12 and 13 are applied and attached to the absorbent article intermittently during the manufacturing process. Alternatively the outer leak barriers 13 may be applied continuously and are then cut away in the crotch region 4 when the cuts for the leg openings 5a, 6a are made. In the latter case the distance between the outer leak barriers may exceed the narrowest crotch width, e, wherein all of the outer leak barriers 13 are cut away in said area. Alternatively the distance between the outer leak barriers is slightly smaller than the narrowest crotch width, e, so that a part of the area adjacent the distal edges 13b, including the elastic member 18, of the outer leak barriers 13 will remain and be attached to the inner cover 10 so as to form leg elastics in a manner described above.

The absorbent article shown in FIG. 1 is, as mentioned above, designed as an absorbent pad to be used in a pair of pants. It may in a known manner be provided with fastening means in the form of adhesive strings on the outside of the outer cover to be fastened to the panties. It is however understood that the absorbent article may be of any other known type, such as a diaper or an incontinence garment, intended to be fastened together around the waist of the wearer by fastening means, such as adhesive tape or hook-and-loop fasteners, to assume a pant-like shape. The article may also be a belted article having belt members attached to the back region for fastening the article around the waist of the wearer. The article may further be provided with additional features, such as leg elastics, waist elastics etc.

Figure 5:
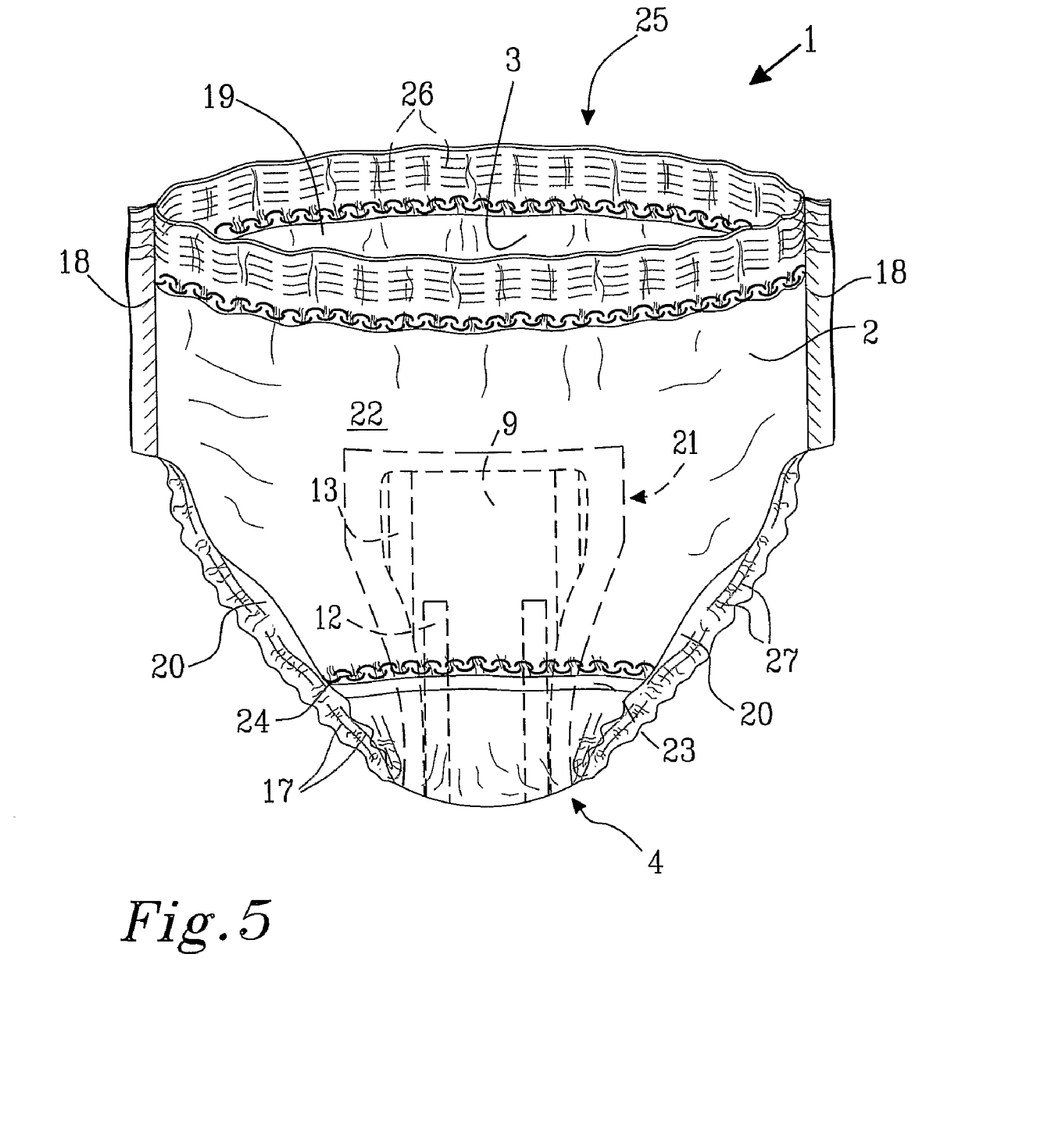
FIG. 5 shows a perspective view of a pant diaper.
Figure 6:
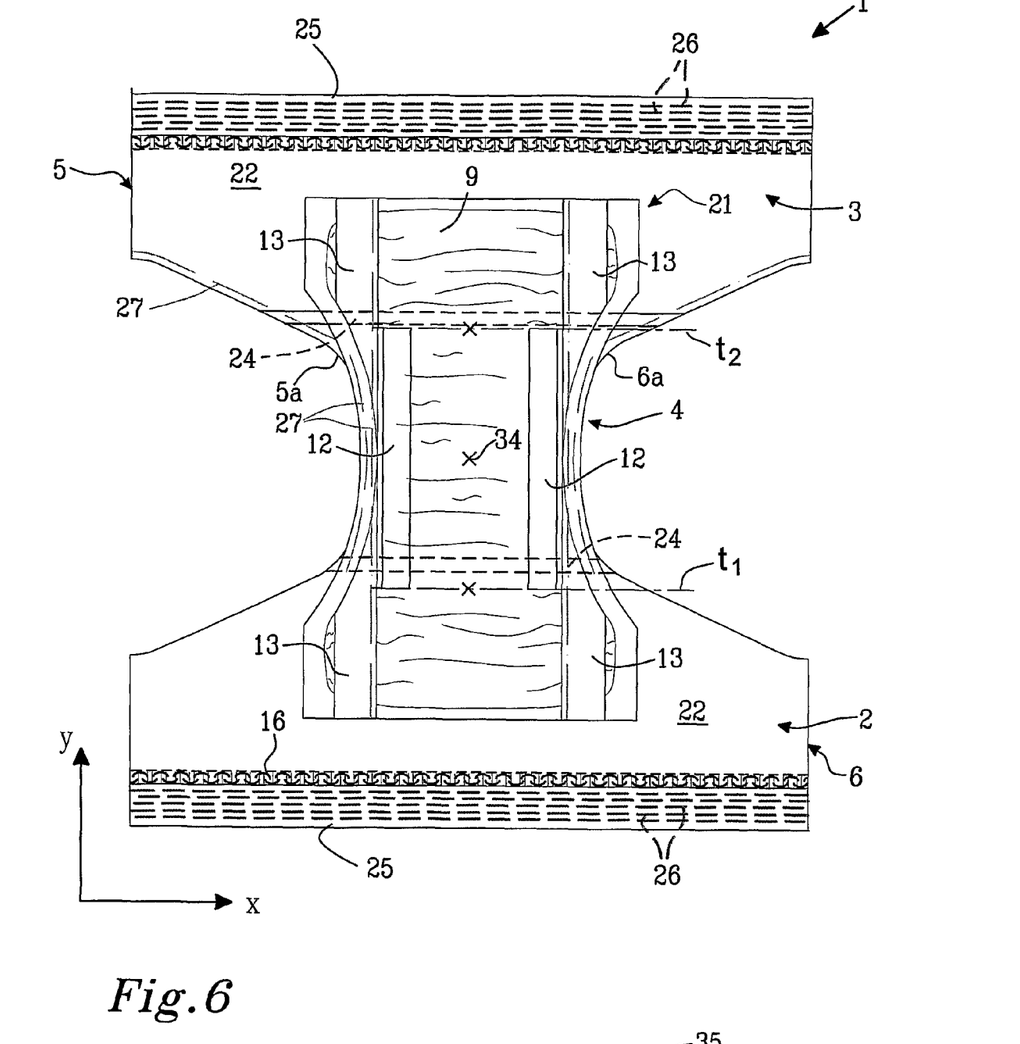
FIG. 6 shows is a plan view of the pant diaper in its flat, uncontracted state prior to formation as seen from the body facing side.

The article may also be a pant article, such as a pant diaper, a sanitary pant or an incontinence pant. One example of a pant-type absorbent article is shown in FIGS. 4 and 5. The front and back panels 2 and 3 of the pant article are joined to each other along their longitudinal side edges thereof forming side seams 18 to define a waist-opening 19 and a pair of leg-openings 20.

The pant article shown in FIGS. 4 and 5 comprises a core region 21 comprising the absorbent core 9, a liquid pervious inner cover 10 and a liquid impervious outer cover 11 as disclosed above, and a chassis region outside the core region 21. The chassis comprises a front region 2, a back region 3 and a waist region comprising an elastic waistband 25. At least a part of the chassis region comprises a coversheet 22 of a soft and comfortable material in the form of an elastic web material, for example an elastic laminate. An example of such a pant article is disclosed in WO2005/122985 and WO2006/093439. Further details about the elastic laminate used as coversheet 22 may be found in any of these documents.

Further examples of elastic laminates are stretch-bonded laminates in which a nonelastic material is joined to an elastic material while the elastic material is in a stretched condition, so that when the elastic material is relaxed, the nonelastic material gathers between the locations where it is bonded to the elastic material. It is also known to laminate (or bond) a necked material to an elastic sheet to produce a neck bonded laminate which is capable of stretch and recovery in the cross-machine direction. This process involves an elastic member being bonded to a non-elastic member while only the non-elastic member is extended in one direction (usually the machine direction) and necked in the transverse direction, so as to reduce its dimension in the direction orthogonal to the extension. It is further known to utilize intermeshing grooved rolls or discs for stretching nonwoven webs. For instance, it is known to use grooved rolls generally to stretch a laminate formed from an elastic and a non-elastic (extendable) web, for example a nonwoven, in order to form an elastic laminate.

The elastic laminate 22 may cover the entire article, including the core region 21 and the entire front and back panels 2 and 3. However according to a preferred embodiment a substantial part of the crotch region 4 of the article is free from the elastic web material 22. A "substantial part" used herein refers to at least 50%, preferably at least 75%.

A crotch region web material 23, which preferably is a non-elastic nonwoven material, is arranged in the crotch region 4 of the article and overlaps with the elastic front and back panels 2 and 3. The crotch region web material 23 is joined in an overlapping manner to the front and back panels 2 and 3, respectively, by means of ultrasonic welds 24, heat bonding, cold bonding, glue strings or the like.

An elastic waist band 25 is further provided which comprises a substantially non-elastic nonwoven material that is elasticized by elongate elastic members 26 such as elastic threads, contractably affixed between material layers, such as nonwoven materials. Elastic threads 27 may also be arranged around the leg openings 5 and 6 of the article.

The liquid-impervious backsheet material 11 underlies the absorbent core 9 and adjacent areas immediately outside the absorbent core 9. The area covered by the liquid-impervious backsheet 11 is defined as the core region 21. The crotch nonwoven material 23 is arranged on the garment-facing side of the liquid-impervious backsheet 11 in the crotch region 4 of the article. The core region 21 extends into the front and back panels 2 and 3 so that the elastic web material 22 and the liquid impervious backsheet 11 overlap in the outer parts of the core region 21, wherein the elastic web material 22 is arranged on the garment facing side of the liquid impervious backsheet 11.

In one embodiment the surface area of the absorbent core 9 amounts to no more than 50%, preferably not more than 40%, of the total surface area of the article, as measured in a flat state of the article. The elastic laminate 22 constitutes the sole component of at least parts of the front and back panels 2 and 3.

No additional elasticized side panels joining the front and back panels 2 and 3 are needed when using the elastic laminate 22.

Inner leak barriers 12 are arranged in the crotch region 4 of the pant article and extend alongside the absorbent core 9. Outer leak barriers 13 extend alongside the wider part of the absorbent core 9 in the front region 2 and the back region 3 of the article, while at least a main part of the crotch region 4, along which the inner leak barriers 12 extend, is free from outer leak barriers 13. There are preferably no outer leak barriers present in the areas of the front and back region which are outside the core region 21.

The invention may be applied to any type of absorbent article having raised leakage barriers. It is especially useful in articles having a relatively big difference in the width of the absorbent core in the crotch region and the front and/or back regions respectively as described above. One advantage of the present invention is that it provides an improved utilization of the absorbent core and thus reduces the risk for leakage. It further provides and improved comfort and fit and suits female as well as male wearers. For female wearers absorbent capacity is mainly needed in the crotch region and the back region, while for male wearers absorbent capacity is mainly needed in the front and the crotch regions.

It should be understood that several modifications of the inventions are possible within the scope of the claims.

The invention claimed is:

1. An absorbent article comprising:
    an absorbent core;
    a body facing liquid receiving surface;
    a liquid impervious garment facing surface;
    said article having a longitudinal direction and a transverse direction and being defined by a pair of longitudinal side edges and a pair of transverse side edges;
    said article comprising, as seen in its longitudinal direction, a front region, a back region and a crotch region therebetween;
    a body facing side of said article further comprising substantially longitudinally extending inner and outer leak barriers, each of said inner and outer leak barriers having a free laterally inward elasticized side arranged at their distal longitudinal edges and a laterally outward side arranged at their proximal longitudinal edges, the elasticized sides of the leak barriers the body facing liquid receiving surface, said distal longitudinal edge of said inner leak barrier being substantially parallel with said distal longitudinal edge of said outer leak barrier,
    wherein said inner and outer leak barriers are located alongside each side of the absorbent core, said inner and outer leak barriers being spaced from each other in the transverse direction of the article, wherein the inner leak barriers extend at least along the part of the crotch region having a smallest width in the transverse direction, and along a length of at least 5 cm, and the outer leak barriers extend along at least a part of at least one of the front region and the back region of the article, while at least a part of the crotch region along which said inner leak barriers extend is free from raised outer leak barriers.

2. The absorbent article as claimed in claim 1, wherein said inner leak barriers extend along a length of at least 8 cm.

3. The absorbent article as claimed in claim 1, wherein at least a substantial part of the front and back regions are free from said inner leak barriers.

4. The absorbent article as claimed in claim 3, wherein said inner leak barriers extend along a length of no more than 30 cm.

5. The absorbent article as claimed in claim 1, wherein there is an overlap in the longitudinal direction between the inner and outer leak barriers of between 0.5 cm and 10 cm.

6. The absorbent article as claimed in claim 1,
wherein the inner leak barriers have a height as measured from the free laterally inward elasticized side edge and the opposite laterally outward side edge attached to the inner cover of between 1 and 5 cm.

7. The absorbent article as claimed in claim 1,
wherein the outer leak barriers have a height as measured from the free laterally inward elasticized side edge and the opposite laterally outward side edge attached to the inner cover of between 1 and 8 cm.

8. The absorbent article as claimed in claim 1,
wherein the laterally inward elasticized side of the outer leak barriers extend along at least part of the crotch region, but is deactivated in at least part of said region by being attached to the inner cover of the article, thus preventing it to raise.

9. The absorbent article as claimed in claim 8,
wherein the laterally inward elasticized side of the outer leak barriers extend along the crotch region in said deactivated state over a length at least 5 cm, in the longitudinal direction of the article.

10. The absorbent article as claimed in claim 1,
wherein the absorbent core in the crotch region has a smallest width in the transverse direction of no more than 20 cm.

11. The absorbent article as claimed in claim 1,
wherein the absorbent core has a largest width in the front or back region which is at least 20% larger than the smallest width of the absorbent core in the crotch region of the article.

12. The absorbent article as claimed in claim 1,
wherein the outer leak barriers are present in both the front and the back regions of the article.

13. The absorbent article as claimed in claim 1,
wherein said article is a pant type absorbent article, said article having a core region comprising an absorbent core, and a chassis surrounding the core region, said chassis comprising front, back and waist regions, wherein the core region is located at least in the crotch region of the article, a liquid impermeable outer cover is arranged at least in the core region on the garment-facing side of the absorbent core and a liquid permeable inner cover is arranged at least in the core region on the wearer-facing side of the absorbent core, and said article in at least a part of the chassis region comprises an outer coversheet in the form of an elastic web material.

14. The absorbent article as claimed in claim 13,
wherein the inner and outer leak barriers are arranged in the core region of the article.

15. The absorbent article as claimed in claim 13,
wherein the surface area of the absorbent core amounts to no more than 50% of the total surface area of the article, as measured in a flat state of the article.

16. The absorbent article as claimed in claim 2, wherein said inner leak barriers extend along a length of at least 15 cm.

17. The absorbent article as claimed in claim 4, wherein said inner leak barriers extend along a length of no more than 25 cm.

18. The absorbent article as claimed in claim 5, wherein the overlap in the longitudinal direction between the inner and outer leak barriers is between 1 cm and 5 cm.

19. The absorbent article as claimed in claim 10, wherein the smallest width is no more than 18 cm.

20. The absorbent article as claimed in claim 11, wherein the largest width in the front or back region which is at least 30% larger than the smallest width of the absorbent core in the crotch region of the article.

21. The absorbent article as claimed in claim 13, wherein the article is a pant diaper, a sanitary pant or an incontinence pant.

22. The absorbent article as claimed in claim 15, wherein the surface area of the absorbent core amounts to no more than 40% of the total surface area of the article, as measured in a flat state of the article.

* * * * *